United States Patent
Valentini et al.

(10) Patent No.: US 6,761,289 B1
(45) Date of Patent: Jul. 13, 2004

(54) PREPARATION AND METERING OF COMPONENTS MIXED WITH $CO^2$

(75) Inventors: Giorgio Valentini, Pisa (IT); Claudio Menicagli, Pisa (IT)

(73) Assignee: Abiogen Pharma S.p.A., Pisa (IT)

( * ) Notice: Subject to any disclaimer, the term of this patent is extended or adjusted under 35 U.S.C. 154(b) by 183 days.

(21) Appl. No.: 10/018,910

(22) PCT Filed: Jun. 21, 2000

(86) PCT No.: PCT/EP00/05729

§ 371 (c)(1),
(2), (4) Date: Dec. 18, 2001

(87) PCT Pub. No.: WO01/00507

PCT Pub. Date: Jan. 4, 2001

(30) Foreign Application Priority Data

Jun. 25, 1999 (IT) .......................................... MI99A1416

(51) Int. Cl.[7] .............................................. B65D 83/14
(52) U.S. Cl. ...................................... 222/402.1; 222/1
(58) Field of Search ................................... 222/1, 402.1

(56) References Cited

U.S. PATENT DOCUMENTS 3,947,568 A * 3/1976 Bates et al. .................... 424/47

FOREIGN PATENT DOCUMENTS

GB         1449272 A * 9/1976 ........... C09K/03/30

* cited by examiner

*Primary Examiner*—Kenneth Bomberg
(74) *Attorney, Agent, or Firm*—Bucknam & Archer

(57) ABSTRACT

A method is described for preparing mixtures of salts and/or other substances in general, including calcium and magnesium salts with carbon dioxide in pressurized containers, for the purpose of producing systems for the delivery of said mixtures in soluble form and at a predetermined and constant saline concentration, for a wide variety of applications. The mixtures containing the substances are prepared in a stirred reactor under a pressure of carbon dioxide, and from there are brought into use after they have been transferred into containers that are suitable for maintaining the internal pressure generated by the carbon dioxide in the form of vapor, in the form of a liquid/vapor mixture or under supercritical conditions.

10 Claims, No Drawings

PREPARATION AND METERING OF COMPONENTS MIXED WITH CO²

FIELD OF THE INVENTION

The present invention relates to pressurized containers containing additives for water, beverages or foods and carbon dioxide. The containers of the invention are useful for metering additives an soluble form and of predetermined and constant saline concentration.

Pressurized carbon dioxide serves to promote the formation of water-soluble species, for example in the case of calcium and magnesium salts in the form of bicarbonates, and, simultaneously, to act as a propellent when the dispensing system is opened.

This method also has the advantage of not requiring the addition of preserving agents to the preparations, given the sterilizing action exerted by carbon dioxide on the components of the mixture.

Mixtures containing additives are prepared in a stirred reactor under a pressure of carbon dioxide, and from there are transferred into containers that are suitable for maintaining the internal pressure generated by the carbon dioxide in the form of vapour, in the form of a liquid/vapour mixture or under supercritical conditions.

Carbon dioxide performs a multitude of functions: reagent, preserving agent, propellent and, finally, solvent, in virtue of its low condensation pressure (6.5 MPa at 20° C.).

The present invention is able to respond to the demands of all situations requiring:

the modification of the chemical nature and behaviour of the substances in the mixture;

the preservation of the substances to be dispensed in an inert and/or sterile atmosphere;

metering in an automatic or time-controlled mode or in a mode linked to the control of process parameters;

the dispersal of the substances added in the receptor means.

One of the fields in which there are requirements of particular importance and for which there are currently no adequate highly-automated solutions is that of the supplementation of salts or other chemical substances or preparations intended for:

1. water for aquaria (for example metering of salts);
2. water for consumption (for example metering of salts);
3. water for therapeutic or thermal use;
4. water for industrial use (for example metering of additives of various types);
5. water for agricultural or animal-rearing use (for example metering of nutrients, drugs or phytopharmaceuticals);
6. supplementation of foods and beverages intended for either human or animal consumption;
7. extemporaneous preparation of dietary drinks and/or beverages in general.

PRIOR ART

According to the conventional technique, when it is necessary to form any liquid preparation in which a plurality of salts or chemical substances are present in solutions, typically aqueous solutions, under conditions of controlled concentration, the solution generally consists in adding saline mixtures or other components in the form of powders, tablets or the like.

These methods cannot be used when a simultaneous metering needs to be made of substances which have different solubilities or solubilization rates or when some of these substances are actually sparingly soluble, such as many calcium and magnesium salts.

The main fields in which requirements for the metering of calcium and magnesium in aqueous solution are identified are, schematically:

production of foods or beverages;

production of drugs for the treatment and prophylaxis of diseases, such as hypocalcaemia, osteoporosis, etc., which require the supplementation of calcium;

conditioning of water to be made suitable for consumption or for given technological or applied uses (for example for particular types of aquarium).

In all these cases, the solutions offered by the prior art are entirely unsuitable for use to obtain mineralized waters, in particular mineralized with calcium and magnesium.

Thus, when there is a need to have concentrations of calcium, magnesium and bicarbonate ions at levels comparable with those usually found in waters intended for human consumption, or even higher levels, such as in the case of aquaria, in which it is necessary to have calcium and magnesium concentrations that are constant over time, the problems relating to the metering of these ions are associated with the natural difficulty of dissociating many of their salts in water.

Various solutions have been put into practice for this purpose, which are at times characterized by a certain degree of complexity.

Some of the solutions proposed involve the use of ceramic material, in the form of filters or pellets, or of calcium carbonates mainly of mineral origin (for example calcite, aragonite, etc.) alone or mixed with the corresponding magnesium salts in the form of fixed beds of varied conformation and structure (mainly in the form of columns or cartridges) used as sources for the release of the salts in solution following lixiviation by the water to be enriched.

One adopted system consists in adding carbon dioxide to the water immediately before it is placed in contact with the fixed bed. This type of process is based on the solubilizing action of carbon dioxide on calcium salts, according to the known equilibrium:

$$CaCO_3(s) + H_2O + CO_2 \rightarrow Ca^{2+} + 2HCO_3^-$$

given that calcium carbonate is insoluble and calcium bicarbonate (which does not exist in solid form under ordinary conditions) is soluble in water.

On the other hand, the solubility of calcium carbonate as a function of the pH can be represented schematically as follows:

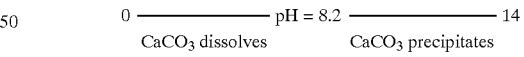

such that the action of the carbon dioxide, by consequently lowering the pH of the solution, brings about its dissolution.

As an alternative to methods involving the use of carbonates, it is possible to use partially soluble calcium and magnesium salts, such as the respective oxides or hydroxides, with which saturated solutions are generally produced, the homogeneous part of which can be used directly following separation from the residual material.

In this case also, the use of pressurized carbon dioxide, fed separately into the reactor in which the dissolution of salts is carried out, allows better exploitation of the saline preparation.

The reaction which takes place is as follows, which brings about the dissolution of calcium here too:

$$Ca(OH)_2 + 2CO_2 \rightarrow Ca^{2+} + 2HCO_3^-$$

The insoluble residue which remains after the treatment can in turn be converted into bicarbonate (soluble salt) by further treatment with carbonated water.

On the whole, this is relatively difficult to achieve.

Independently of the type of matrix used as the source of calcium or magnesium, the existing applications still suffer from a series of considerable limitations.

In the case of processes starting with carbonates, the objective simplicity of the plants comes up against an appreciable difficulty in ensuring a constant result in terms of concentration of the dissolved salts, especially in processes which do not involve rigorously continuous control.

Although the use of oxides or hydroxides ensures the possibility of a more reliable control of the process both under continuous and batchwise conditions, this approach involves decidedly greater production-plant complexity.

Using soluble calcium and magnesium salts (for example the respective chlorides) alone or in mixtures thereof, it is possible to obtain the respective solutions, although these are considerably acidic (due to the hydrolysis of the salt) and above all have high concentrations of chloride ions, which is often unsuitable for many applications.

In addition, in the presence of other soluble salts, such as sodium bicarbonate or potassium bicarbonate, even those calcium and/or magnesium salts that are individually very soluble in water, such as, the chlorides or nitrates, result in the spontaneous formation of the corresponding insoluble carbonates.

The metering of these mixtures would then result in the incomplete solubilization of the salts, or else, for low levels of salinity, relatively long times and prolonged stirring would be required to obtain a clear solution.

When it is desired to prepare a "synthetic water", by adding salts to water having low salt content, or when it is simply desired to supplement calcium and magnesium salts into ordinary waters, difficulties are encountered since generally a solid precipitate forms, due to the incomplete solubilization of the added salts.

DESCRIPTION OF THE INVENTION

The method object of the present invention consists in preparing pressurized containers with which waters and foods, beverages, drinks, even dietetic ones, can be produced and supplemented, by means of the combined metering of the carbon dioxide and the additives, which are capable of dissolving instantaneously once introduced under pressure into the aqueous phase.

According to the various applications, the additives can be prepared as an aqueous solution or suspension, while the carbon dioxide can be present in the form of vapour, a liquid/vapour mixture or a supercritical fluid.

The packaging in pressurized containers allows easy transportation and use by means of devices for metering of the contents.

Examples of additives which can be used in accordance with the invention comprise:

inorganic salts, in particular calcium and/or magnesium salts;

components of drinks to be prepared immediately before use, such as flavourings, fruit extracts, sweeteners, sugars and colourings.

For the mineralization of waters (drinking waters, waters for aquaria, waters for industrial use or the like), in addition to magnesium and/or calcium oxides, potassium and sodium salts may be present as well, preferably potassium sulphate, sodium bicarbonate, and optionally chlorides.

On the other hand, calcium carbonate can be used in the containers of the invention for the supplementation of foods such as milks and yoghurt.

Depending on the applications, the containers of the invention will contain, by way of example, one or more of the following salts, in the indicated amounts: 1 to 1000 mg of calcium carbonate, 1 to 800 mg of magnesium carbonate, 1 to 1000 mg of sodium bicarbonate, 1 to 800 mg of potassium bicarbonate, 1 to 600 mg of potassium sulfate, 1 to 500 mg of sodium sulfate, 1 to 300 mg of sodium chloride, 1 to 300 mg of potassium chloride, 1 to 100 mg of sodium nitrite, 1 to 100 mg of potassium nitrite, 1 to 50 mg of other specific oligoelements (such as iron, fluorides, selenium and the like) and 1 to 50 g of carbon dioxide.

The combinations of anions and cations of the various salts can of course be different from those listed above.

Before being introduced into the containers, the salts can be optionally subjected to lyophilization and micronization.

The invention proposed is characterized by considerable simplicity, easy implementation and by the fact that it overcomes the problems which distinguish the known technical solutions in processes of either continuous or batchwise type.

In particular, the invention is particularly advantageous when there is a need to have bicarbonate ions together with calcium or magnesium ions in large amounts and in a uniform and constant manner in waters intended for human consumption, as is found in natural waters, as well as in the case of aquaria, in which there is a need to have relatively high concentrations of said salts which remain constant over time.

Specifically, this invention makes it possible to exploit the action of carbon dioxide under pressure in order to displace the carbonate-bicarbonate equilibrium and to carry out a conversion of the salts present in the mixtures already during the preparation of these mixtures, in a manner such that the salts are in a form which is more rapidly soluble at the time of metering.

The pressurized carbon dioxide performs many functions:

solvent, on account of its low condensation pressure (6.5 MPa at 20° C.)

reagent, since it displaces the equilibrium of the saline systems towards the formation of calcium bicarbonate, which is extremely soluble;

propellent, in that it allows the discharge of the salt in the form of finely divided powder, or of a homogeneous liquid solution which is more or less viscous or of a solid/liquid mixture (even of pasty consistency);

agent for mixing the aqueous medium which receives the substances delivered by the pressurized container, promoting their dispersion or solubilization;

preserving agent, for example for sugar products or other organic compounds which deteriorate readily.

The mixtures are prepared in a stirred reactor, into which the salts and the other components of the mixture are initially fed, optionally in the presence of a certain amount of water; the components can in fact be introduced into the mixture in the form of finely divided powder, or in saturated aqueous solution (solid/liquid suspension or paste).

The reactor is then pressurized with carbon dioxide to increasing pressure values, generally of between 3 Mpa and 7 Mpa, until the processes of conversion/stabilization of the components introduced have occured; this process can also require a "maturation" time of a few hours.

The resulting mixtures are transferred from the reactor into a certain number of pressurized containers, of suitable shapes and sizes, which can optionally also operate at a pressure lower than that in the primary reactor.

The total amount of salts loaded into the first reactor depends on the number of containers to be filled; for example, when using salts in amounts ranging from 10 to 500 g total salts, 10 to 2000 containers can be filled, depending on the intended applications.

The loading of said containers takes place by exploiting the carbon dioxide pressure inside the reactor, optionally following creation of a vacuum inside the receiving container.

Optionally, the carbon dioxide pressure in the pressurized container can be increased after loading by feeding in carbon dioxide at higher pressure.

In the case of the preparation and/or supplementation of dietary drinks and beverages, suitable cartridges are used in which the insertion of the various ingredients can be carried out by loading the substances other than the carbon dioxide either as powders or as aqueous syrups prepared beforehand.

The first system consists in adding to the empty cartridge a finely divided and dispersed mixture of the components to be measured out and then loading the carbon dioxide up to the desired pressure.

Said cartridges will contain, by way of example, 0.5 to 2 g of fruit dehydrated extracts (such as powder orange), 0.5 to 2 g of flavours (such as orange flavour, lemon flavour, etc.), 0.5 to 2 g taste enhancers (such as citric acid), 0.1 to 1 g of sweeteners (such as acesulfame K, sodium saccharinate), 0.02 to 0.1 g of dyes (such as beta-carotene), optionally 0.1 to 0.5 of calcium and/or magnesium salts or other soluble salts and 1 to 10 g of carbon dioxide.

In order to achieve an instantaneous dissolution of the components at the time of their delivery into the water, the components can be lyophilized and finely divided beforehand, so as to be readily dispersed during the delivery of the carbon dioxide.

Finally, alternatively, an aqueous syrup containing all the necessary ingredients can be prepared separately. This syrup, which is extremely viscous, is loaded into the empty cartridge before the latter is pressurized with carbon dioxide.

The method can be applied to the preparation of single-dose pressurized cartridges containing all the salts and/or substances in general, of the type usually used for the preparation of soda water by making use of the respective "soda siphon".

Alternatively, this preparative technique can be used for the production of multi-dose aerosol cans, which can be used for example for the preparation of instant beverages by means of direct metering into a glass of water or some other known volume.

By following the two preparation alternatives described above, multi-dose containers can also be produced, which are larger in size than the aerosol cans described previously.

These containers will be equipped with an autonomous delivery system which allows the metering, if required, also directly into a glass.

For this application, the ability of carbon dioxide to create an inert and sterile atmosphere is exploited, which makes it possible to formulate the preparation contained in the pressurized container without the use of preserving agents and to keep it at room temperature for a long time without any adverse change in its organoleptic properties, thus making it possible to deliver single doses repeatedly over time.

The method of the invention makes it possible to insert into a single cartridge pressurized with carbon dioxide all the components which allow either the supplementation of water, foods and beverages or the extemporaneous preparation of drinks and beverages of various types.

As regards this last sector, the production of beverages with given taste and flavour characteristics has been carried out hitherto by means of the addition to water of the basic components (flavourings, flavour enhancers, natural essences, sweeteners, stabilizers, antioxidants, etc.), in the form of sugary powdered products or syrups (sugary concentrates).

However, in both cases, manual stirring of the aqueous mixture is required in order to ensure solubilization of the components added.

In addition, whenever a carbonated beverage is required or desired, the main techniques currently used involve a carbonation step which always follows that of addition of the effervescent solid mixtures or of the commercial sugary syrups.

However, under these conditions, following the introduction of the carbon dioxide, the conventional mixtures produce a large amount of long-lasting foam, creating unsuitable conditions for consumption for several minutes; it is thus necessary to wait a certain amount of time before the beverage can be consumed. However, during this time, some of the effervescence of the preparation is lost.

This in fact hampers the production of carbonated beverages which can be prepared extemporaneously.

By virtue of the choice of suitable saline and sugar constituents which are capable of dissolving instantaneously under the conditions of delivery/metering in water, the present invention allows the extemporaneous preparation of dietary beverages with a large variety of tastes, overcoming the problems associated with the dissolution of its components and in particular avoiding the formation of long-lasting foams.

In the case especially of the supplementation of calcium and magnesium, the salts dosed according to the invention dissolve very quickly (virtually instantaneously in most applications), thus making it possible, very simply and reliably, to plan and manage the control and automation of the control of the metering, which can be achieved by means of a probe capable of measuring the dissolved calcium or, in a non-specific but nevertheless representative manner, the electrical conductivity of the solution.

The method proposed thus has wide versatility of use and offers appreciable advantages since it allows:

the preparation of real and genuine "synthetic" mineral waters by integral addition of salts to waters of low salinity such as rain waters or waters obtained from osmosis, distillation or condensation processes or by dissolving natural snow or ice, and intended for consumption by humans or animals or for irrigation;

the preparation of waters intended for animal rearing or animal life (for example for aquaria) or for plant crops;

the correction of the technological properties of process waters (corrosiveness);

the modification of the taste properties of waters, beverages and foods;

the correction of aqueduct or well waters to bring them within predetermined quality standards;

the preparation of waters for irrigation use with particular ratios between the saline components for purposes such as agronomy and/or research;

the improvement in the usability of natural waters for given uses such as the formulation of waters which need to have characteristics equal to sea water, thermal waters, geothermal waters, etc.;

the extemporaneous preparation of drinks and beverages, including dietary ones;

the preparation of mixtures intended for preparing drinks and beverages without the use of preserving agents or antioxidants;

the production of a large variety of beverages or infusions immediately ready for consumption without the formation of foams;

the preparation of products for food or therapeutic or dietary use, including saline supplements.

The examples which follow illustrate the invention in greater detail.

EXAMPLE 1

A mixture of calcium oxide and demineralized water is pressurized with carbon dioxide up to a pressure of 3–7 MPa typically 5 MPa) and is maintained under these conditions for at least 12 hours.

The addition of this mixture to 1 liter of demineralized water, in an overall proportion of 250 mg of solids, delivered directly into the liquid to ensure the participation of carbon dioxide in the dissolution phases, produces a clear homogeneous solution with a content of calcium in solution equal to 179 mg/liter.

EXAMPLE 2

A mixture of magnesium oxide and demineralized water is pressurized with carbon dioxide up to a pressure of 3–7 MPa (typically 5 MPa) and is maintained under these conditions for at least 12 hours.

The addition of this mixture to 1 liter of demineralized water, in an overall proportion of 150 mg of solids, produces a clear homogeneous solution with a content of magnesium in is solution equal to 90 mg/liter.

EXAMPLE 3

A mixture of salts having the following percentage weight composition:

| | |
|---|---|
| $CaCl_2$ | 9.0 |
| $CaO$ | 6.8 |
| $NaHCO_3$ | 76.7 |
| $MgO$ | 7.5 | is placed in demineralized water and then pressurized with carbon dioxide up to a pressure of 3–7 MPa (typically 5 MPa) and maintained under these conditions for at least 12 hours.

The addition of this mixture to 1 liter of demineralized water, in an overall proportion of 730 mg of solids, produces a clear homogeneous solution with the following ionic composition in mg/liter:

| | |
|---|---|
| $Ca^{2+}$ | 59 |
| $Na^+$ | 153 |
| $Mg^{2+}$ | 33 | which correspond to concentrations that are entirely common for natural waters.

EXAMPLE 4

A mixture of salts having the following percentage weight composition:

| | |
|---|---|
| $CaCl_2$ | 7.9 |
| $CaO$ | 49.0 |
| $NaHCO_3$ | 35.8 |
| $MgO$ | 5.3 |
| $K_2SO_4$ | 2.1 | is placed in demineralized water and then pressurized with carbon dioxide up to a pressure of 3–7 MPa (typically 5 MPa) and is maintained under these conditions for at least 12 hours.

The addition of this mixture to 1 liter of demineralized water, in an overall proportion of 235 mg of solids, produces a clear homogeneous solution with the following ionic composition in mg/liter:

| | |
|---|---|
| $Ca^{++}$ | 89 |
| $Na^+$ | 23 |
| $Mg^{++}$ | 7.5 |
| $K^+$ | 1.1 |

EXAMPLE 5

1 liter of an orange-flavoured dietary beverage is prepared by using a standard stainless steel cartridge of the type used for the preparation of soda water. A cartridge with a free volume of 10 cm$^3$ is prepared so as to contain:

| | |
|---|---|
| Orange powder 150 CD New Food: | 1.60 g |
| Orange flavour 10950-31 G-R: | 1.00 g |
| Anhydrous citric acid (flavour enhancer): | 1.00 g |
| Acesulphame K (artificial sweetener): | 0.35 g |
| Powdered beta-carotene (colouring) : | 0.064 g |

The mixture is then pressurized with carbon dioxide of technical-grade purity, up to saturation with a pressure of about 6.5–7 MPa. Under these conditions, the cartridge contains about 8 g of liquefied carbon dioxide, which is sufficient to produce 1 liter of beverage in a soda siphon from which the beverage can be delivered into a glass by exploiting the propellent action of the gas, without forming long-lasting foams.

EXAMPLE 6

As described in Example 5, but with the following doses:

| | |
|---|---|
| Orange powder 150 CD New Food: | 1.60 g |
| Orange flavour 10950-31 G-R: | 1.00 g |
| Anhydrous citric acid (flavour enhancer): | 1.00 g |
| Sodium saccarinate (artificial sweetener): | 0.075 g |
| Powdered β-carotene (colouring) | 0.064 g |

EXAMPLE 7

70 g of calcium carbonate are placed in one liter of water and pressurized with carbon dioxide up to a pressure of 3–7 MPa and maintained under these conditions for at least 12 hours.

The addition of 8 ml of this mixture to 200 ml of milk (about a tumbler-full) produces a 560 mg increase in calcium to the 240 mg of calcium naturally present in the milk sample and the RDA value of the calcium rises from 30% to 100%; in practice, a single daily intake (one glass of milk) provides all the daily requirements of calcium.

EXAMPLE 8

77.5 g of calcium carbonate are placed in one liter of water and pressurized with carbon dioxide up to a pressure of 3–7 MPa and maintained under these conditions for at least 12 hours.

The addition of 8 ml of this mixture to 150 g of yoghurt (about one commercial pot-full) allows a 620 mg increase in calcium to the 180 mg of calcium naturally present in the yoghurt sample, and the RDA value of the calcium rises in this way from 22.5% to 100%; in practice, a single daily intake (one pot of yoghurt) provides all the daily requirements of calcium.

What is claimed is:

1. A pressurized container containing calcium and magnesium oxides, in powder form or saturated aqueous solution, and carbon dioxide, said calcium and magnesium oxides dissolving instantaneously when introduced under pressure in an aqueous phase.

2. The pressurized container as defined in claim 1, which further contains sodium and potassium salts.

3. The pressurized container as defined in claim 2, wherein the sodium and potassium salts are sodium bicarbonate and potassium sulphate.

4. The pressurized container as defined in claim 1, in the form of a single-dose cartridge or aerosol can.

5. The pressurized container as defined in claim 1, in the form of a multi-dose cartridge or an aerosol can.

6. A pressurized container containing calcium and magnesium carbonates, in powder form or saturated aqueous solution, and carbon dioxide, said calcium and magnesium carbonates dissolving instantaneously when introduced under pressure in an aqueous phase.

7. The pressurized container as defined in claim 6, which is further contains sodium and potassium salts.

8. The pressurized container as defined in claim 7, wherein the sodium and potassium salts are sodium bicarbonate and potassium sulphate.

9. The pressurized container as defined in claim 6, in the form of a single-dose cartridge or an aerosol can.

10. The pressurized container, as defined in claim 6, in the form of a multi-dose cartridge or an aerosol can.

* * * * *